United States Patent [19]

Papandrea

[11] Patent Number: 5,527,779
[45] Date of Patent: Jun. 18, 1996

[54] TOPICALLY APPLIED GOLD ORGANIC COMPLEX

[75] Inventor: Ralph A. Papandrea, Collaroy, Australia

[73] Assignee: Top Gold Pty Limited, Collaroy, Australia

[21] Appl. No.: 215,409

[22] Filed: Mar. 18, 1994

Related U.S. Application Data

[63] Continuation of Ser. No. 576,385, filed as PCT/AU89/00118, Mar. 22, 1989, abandoned.

[30] Foreign Application Priority Data

| Mar. 23, 1988 | [AU] | Australia | PI7387 |
| Mar. 28, 1988 | [AU] | Australia | PI7480 |
| Aug. 15, 1988 | [AU] | Australia | PI9878 |
| Jan. 18, 1989 | [AU] | Australia | PJ2313 |

[51] Int. Cl.$^6$ .................. A61K 31/70; A61K 31/705; C07H 11/04
[52] U.S. Cl. ............... 514/23; 514/25; 514/26; 536/17.1; 536/117; 536/121
[58] Field of Search .................. 514/23, 25, 26; 536/17.1, 117, 121

[56] References Cited

U.S. PATENT DOCUMENTS

| 3,635,945 | 1/1972 | Nemeth et al. | 536/17.1 |
| 4,096,247 | 6/1978 | Lantos | 536/117 |
| 4,096,250 | 6/1978 | Hill | 536/118 |
| 4,122,254 | 10/1978 | Hill et al. | 536/121 |
| 4,125,710 | 11/1978 | Hill et al. | 536/121 |
| 4,131,732 | 12/1978 | Hill et al. | 536/121 |
| 4,357,322 | 11/1982 | Rooks, II et al. | 536/53 |
| 4,427,670 | 1/1984 | Ofuchi et al. | 514/174 |
| 4,611,056 | 9/1986 | Guindon et al. | 544/31 |
| 4,617,407 | 10/1986 | Young et al. | 549/462 |
| 4,657,763 | 4/1987 | Finkelstein | 424/131 |
| 4,804,651 | 2/1989 | Duvic et al. | 514/934 |

FOREIGN PATENT DOCUMENTS

WO 85/01653  4/1985  WIPO.

OTHER PUBLICATIONS

D. H. Brown, et al., *Inorganica Chimica Acta*, 93, pp. 141–142 (1984).
D. E. Griswold, et al., *Journal of Rheumatology*, 12,(3), pp. 490–497 (1985).
The Merck Index, Tenth Ed., Windholz et al, issued Oct. 1983 by Merck & Co., Inc. (Rahway, N.J.) see p. 126, cmpd 882.

*Primary Examiner*—Douglas W. Robinson
*Assistant Examiner*—Everett White
*Attorney, Agent, or Firm*—Nikaido Marmelstein Murray & Oram

[57] ABSTRACT

It has been surprisingly found that gold compounds may be applied in topical preparations as an effective treatment of local or systemic inflammatory conditions and/or as antibacterial agents. The present invention therefore relates to new pharmaceutical compositions containing gold for topical application, and the use of the composition in treating inflammation and/or bacterial infection.

28 Claims, No Drawings

TOPICALLY APPLIED GOLD ORGANIC COMPLEX

This is a continuation of application Ser. No. 07/576,385, filed as PCT/AU89/00118, on Mar. 22, 1989, now abandoned.

The present invention pertains to topically applied pharmaceutical compositions of gold compounds and their use in the treatment of psoriasis and as antibacterial agents.

BACKGROUND

Elemental gold was believed in ancient times to have various curative properties. However, in the 1960s the effectiveness of simple inorganic gold salts administered intravenously was demonstrated in the treatment of rheumatoid arthritis. Subsequently, aurothiomalate and aurothioglucose administered in parenteral form were found to be more effective. These are water soluble complexes containing approximately 50% of gold by weight and having thiolate ligands. Gold thiopolypeptide has also been injected. Auranofin, a lipid soluble complex containing approximately 29% of gold by weight and having a phosphine and a sulphur ligand, has been administered orally.

Gold compounds (which term is herein used generally to embrace complexes in which gold is chelated or bound to one or more ligands, organo-gold compounds, inorganic gold compounds and salts thereof) have thus hitherto been administered for therapeutic purposes only by the parenteral or by the oral route and for the treatment of asthma, tuberculosis, pemphigus vulgaris, various forms of arthritis, cancer and infection.

Despite established clinical efficacy, the mechanism of action of gold compounds in the treatment of the above conditions is unknown, although it is appreciated that different chemical forms of gold have varying efficacy with respect to treating the above disorders.

Gold is a transition state metal that is capable of forming complexes in oxidation states I and III, namely:

The chemistry of gold compounds is complicated by the tendency of many compounds to form complex polymers.

Another complication is that gold compounds may undergo extensive modification in the body to produce the active species.

Finally there appears to be no correlation between blood levels of the various gold compounds and biological activity.

The biological activity of gold compounds is not determined solely by the presence of gold itself but also depends on:

a. the oxidation state (I or III)
b. the degree of polymerization
c. the types of ligands
d. the stereochemistry of the molecule Suggested mechanisms for the action of gold drugs include:

a. modulation of humoral and cell-mediated immunity,
b. inhibition of the formation of immune complexes and/or the transmitter substances released as a consequence of the immune complex formation,
c. inhibition of the formation and/or release of lysosomal enzymes,
d. inhibition of the formation and/or action of prostaglandins,
e. inhibition of the proliferation of synovial and other cell types including cancer cells,
f. modulation of copper and zinc metabolism,
g. enzyme inhibition.

Orally administered auranofin exhibits protracted blood levels of gold in comparison with parentally administered gold compounds and is minimally retained in tissue. Both the parenteral and oral routes of administration have been known to produce severe renal, haematological and other adverse effects including skin and mucuous membrane lesions in some cases. Severe gastrointestinal upsets frequently occur following the use of oral gold.

It is known that synovial membrane, particularly when inflamed, may show selective uptake of injected or orally administered gold initially, after which it is distributed to the other tissues.

An example of selective activity is shown by auranofin which possesses greater affinity for penetration of lymphocyte membranes than do many other gold compounds, particularly those of the hydrophilic type.

In 1984 Brown et al applied a water soluble and a lipid soluble gold complex as a solution in ethanol to the skin of rats in order to measure the levels of gold absorbed into the blood stream through topical application [D. H. Brown et al. Inorganica Chimica Acta, 93 L41-L42 (1984)]. It was concluded that the lipid soluble complex was more rapidly absorbed into the blood than the water soluble complex and that blood absorption levels were comparable with oral administration. However, no corresponding tests have been reported on human skin, and studies have not shown correlation between blood levels of gold and clinical effectiveness in treatment of any of the foregoing diseases either in rats or in humans.

It has now been surprisingly discovered that gold compounds administered topically are in some circumstances significantly more effective than gold compounds administered via parenteral or oral routes while avoiding or ameliorating the disadvantages previously discussed.

It has also been surprisingly found that gold compounds administered topically are efficacious in the treatment of local and systemic inflammatory conditions such as psoriasis and rheumatoid arthritis and/or as antibacterial agents.

It has also been found that gold compounds topically applied act synergistically with corticosteroids in the therapeutic treatment of local inflammatory conditions, particularly psoriasis.

SUMMARY OF THE INVENTION

In one aspect the present invention therefore resides in the use of topical applications of a gold compound (as hereinbefore defined) to treat local and systemic inflammatory conditions, particularly psoriasis and rheumatoid arthritis.

According to a second aspect the present invention consists in a composition for topical application comprising a gold compound in combination with a pharmaceutically acceptable carrier having viscosity greater than that of water.

According to a third aspect the invention consists in a method for treatment of the inflamed region of a patient suffering from inflammation comprising the step of applying a gold compound to the skin at or in the vicinity of the inflammation.

Preferably, the gold compounds used in the present invention are lipid soluble.

In a preferred embodiment, the present invention resides in the synergistic mixture of gold compounds and corticosteroids.

The combination of gold compounds and corticosteroids has been surprisingly found to increase therapeutic effectiveness and to also decrease adverse effects.

It has surprisingly also been found that gold compounds are effective against a range of pathogenic bacteria including gram negative and gram positive bacteria, and particularly effective against gram positive bacteria.

BEST METHOD OF PERFORMANCE

The invention will now be more particularly described with reference to specific embodiments by way of example only.

Most gold compounds in use are hydrophilic, a major exception being gold phosphine compounds of the type: $R_3P$—Au—Cl, where R is methyl, ethyl, iso-propyl or n-butyl, $R_3P$—Au—S—R' where R is alkyl, alkoxyl or phenyl, and

R' is H, alkyl, aryl or heterocyclic and may be substituted or unsubstituted.

Preferred R' moieties include substituted carbohydrates and $$-\underset{\underset{CO_2R''}{|}}{CH}-CH_2CO_2R'',$$

wherein R'' is alkyl or H; and $$\begin{array}{c} R_1P-(CH_2)_n-S \\ | \qquad\qquad | \\ Au \qquad\qquad Au \\ | \qquad\qquad | \\ S-(CH_2)_n-PR_3 \end{array}$$

where R, all of which may be the same or different, may be alkyl, aryl or heterocyclic and may be substituted or unsubstituted.

A clinically used example is auranofin:

Preferred compounds for use in the present invention include gold (I) phosphines and related compounds, gold (I) phosphine (or phosphite) thiolates, bis-coordinated gold (I) salts and gold (I) chelates.

The most preferred corticosteroid used in conjunction with gold compounds in a preferred embodiment of this invention is betamethasone dipropionate, although other corticosteroids may be equally as effective.

PHARMACEUTICAL FORMULATIONS

Suitable pharmaceutical formulations for the application of gold compounds to the skin include liquids, powders, gels, ointments, creams, sprays, including metered aerosol sprays, and patches. The choice of formulation depends on the intended therapeutic use.

Choice of formulation for topical use depends on the type and location of the lesion. The formulation may include stabilizers and/or penetration agents or the like. For general topical use a hydrophobic emulsifiable ointment base produces satisfactory results, however, any other formulation for topical application may be equally applicable, for example monohydric, dihydric and trihydric alkanols. The alcohols may be short chain ($C_1$ to $C_{10}$) alcohols or long chain ($C_{12}$ to $C_{20}$) alcohols.

Especially preferred are polyhydric alcohols such as diethylene glycol or glycerol. A simple hydrocarbon base is also effective.

Compounds according to the invention are believed to be efficacious in the alleviation of symptoms of inflammatory disease when applied topically in both humans and animals. It is believed that the compositions are effective at comparatively low concentrations and that therefore the side effects are minimized in comparison with other means of gold administration.

It is further preferred that formulations made in accordance with the present invention may sometimes contain a keratolytic substance, further preferably being salicylic acid. Alternatively, ointments containing heparinoid and hyaluronidase may facilitate absorption of auranofin.

Preferably, the base ointment is a wool alcohol ointment or a simple hydrocarbon base.

EXAMPLE 1

Formulation of Auranofin Ointment

| Ingredients | |
|---|---|
| Ridaura (auranofin) tabs (3 mg) | 60 tabs |
| Alcohol (90%) | 20 mL |
| Propylene glycol | 5 mL |
| Ointment of Wool Alcohols to | 100 g |

Preparation

Ridaura tablets were ground in a glass mortar and alcohol added. This was allowed to soak for 15 min, then ground for 15 min, by which time most of the alcohol had evaporated. Propylene glycol was added and the mixture ground for a further 10 min. The contents of the mortar were weighed and Ointment of Wool Alcohols added to weight.

It is anticipated that commercially prepared auranofin ointment would be made from pure auranofin powder not tablets.

In another preferred method of preparing the ointment, the auranofin powder is triturated with mineral, vegetable or fish oil. The ointment base is then added. The latter can be a pure hydrocarbon base or can contain emulsifying agents such as wool alcohols.

It is well recognized that the formulations in which topical drugs are presented can influence clinical efficacy. The addition of adjuncts such as propylene glycol and urea, can facilitate the extent to which the active drug penetrates the skin.

In inflammatory skin diseases, the barrier to absorption is often disrupted allowing significant systemic absorption of drugs that are normally not absorbed percutaneously. In other skin conditions, intense scaling or lichenification can impede the local penetration of the drug. A similar situation occurs when the condition occurs on the palms and soles. In such cases, the keratolytic agents, either added to the formulation or used prior to treatment with the active drug, may be needed if the drug is to reach its site of action in the skin.

Formulations may be varied depending on the condition and location of psoriatic lesions. A greasy formulation such as those mentioned above are not suitable for application to the scalp. Consequently, the formulation may be varied by those skilled in the art to achieve the desired consistency.

EXAMPLE 2

| Alternative Formulation | |
| --- | --- |
| Propylene glycol | 10 ml |
| Auranofin | 1.8 mg/g |
| Lasonil™ ointment | 14 g |
| Diprosone™ ointment | 15 g |
| Wool Alcohol Ointment to | 90 g |

LASONIL is a trade mark of Bayer and contains 5,000 HDBY heparinoid and 15,000 units of hyaluronidase per 100 g ointment.
DIPROSONE is a trade mark of Schering and contains 0.05% Betamethasone as the dipropionate.

This formulation gives a final concentration of betamethasone dipropionate of approximately 0.008%.

Although only compositions containing Auranofin have been exemplified herein, it is proposed that equivalent compositions containing any one, or a combination of the following gold compounds may be equally effective.

EXAMPLE 3

The preferred gold (I) phosphines and related compounds have the general formula:

$$R_3PAuX \qquad (I)$$

wherein R is alkyl, aryl or heterocyclic, and may be further substituted; and X is halogen.

Preferred examples include $Et_3PAuCl$ and $Ph_3PAuCl$, wherein Ph is phenyl and Et is ethyl.

Compounds of formula I may be prepared by reacting an ethanolic solution of $HAuX_4$ (1 mol) and $R_3P$ (2 mol), or from reacting $AuX$ and $PR_3$. Compounds produced by these methods have high lipid solubility.

Related compounds useful in the performance of the present invention include trialkyl phosphites of the formula:

$$(RO)_3PAuX \qquad (Ia)$$

and thiocynate complexes of the formulae $$R_3PAuSCN \qquad (Ib)$$

and $$(RO)_3PAuSCN \qquad (Ic)$$

wherein R and X are as described above. Preferably R is ethyl or phenyl.

EXAMPLE 4

The preferred gold (I) phosphine (or phosphite) thiolates of the present invention have the general formula:

$$R_3PAuSR^1 \qquad (II)$$

wherein R and $R^1$ may be H, alkyl, aryl or heterocyclic and may be substituted or unsubstituted.

Preferred examples include those in which R is ethyl or phenyl, and $R^1$ is a substituted carbohydrate moiety resulting in compounds such as (IIa)

or (IIb)

wherein X is H, acetyl or formyl; Y is O or S; and n is 1–12.

Another preferred example of this type of compound is $$(C_2H_5)_3PAuS-\underset{\underset{COOC_2H_5}{|}}{CH}-CH_2-COOC_2H_5 \qquad (IIc)$$

The following illustrates a preferred synthetic pathway employed in producing the above compounds:

$$R_3P + AuCl \rightarrow R_3PAuCl$$

$$R_3PAuCl + R^1S^- \rightarrow R_3PAuSR^1 + Cl^-$$

Other examples of appropriate compounds include phosphine or phosphite Au(I) complexes including derivatives of thioalcohols (eg $R_3PAuSCH(R^1)CH(R^2)OR^3$), thioacids (eg $R_3PAuSCH(R^1)CH(R^2)COOR^3$), thiophenols (eg $R_3PAuSC_6H_4R^2$) where $R^1$, $R^2$, $R^3$=H, alkyl, aryl or heterocyclic and may be substituted or unsubstituted. In the case of thiophenols, $R^2$ may be any group eg $NH_2$.

Other examples of suitable compounds of this case include $R_3PAuX$ where X=moieties such as 2-thiazolinyl, thio-2-benzimazolyl and 2-benzoxazolylthio- Large ring chelate compounds such as the following are also suitable compounds $$\begin{array}{c} CH_2-S-Au-P(R_2)-CH_2 \\ | \qquad\qquad\qquad\qquad | \\ CH_2-P(R_2)-Au-S-CH_2 \end{array} \qquad (IId)$$

where R=H, alkyl, aryl or heterocyclic and may be substituted or unsubstituted. Also suitable is $(R_3PAu)_2S$.

EXAMPLE 5

The preferred bis-coordinated gold (I) salts have general formulae of the following type:

$$[R_3PAuPR_3]^+X^- \qquad (IIIa)$$

$$[R_2SAuSR_2]^+X^- \qquad (IIIb)$$

$$[RC_5H_4NAuNC_5H_4R]^+X^- \qquad (IIIc)$$

$[R_3PAuNC_5H_4R]^+X^-$ (IIId)

wherein R is alkyl, aryl or heterocyclic and can be either substituted or unsubstituted; and X is halide, $ClO_4$, $BF_4$ or any monovalent or divalent anion known in the art.

EXAMPLE 6

The preferred gold (I) chelates have the following formula:

(IV)

wherein R is any suitable bridging moiety and may be substituted or unsubstituted alkyl, aryl or heterocyclic; X is O, N or $SO_2NR_2$ and $R^1$ is H, alkyl, aryl or heterocyclic and may be substituted or unsubstituted.

A preferred example is where: R is $C_6H_4$, X is O and $R^1$ is $C_2H_5$.

EXAMPLE 7

Preliminary studies in 19 human subjects with psoriasis showed remarkable therapeutic efficacy and limited signs or symptoms of adverse effects.

One subject was an elderly male with a long history of severe psoriasis that did not respond well to conventional therapy. Under the direction of a dermatologist, auranofin ointment (1.8 mg/g) was applied to a large area of the patient's back and a small area of the left leg. Placebo ointment was applied to the chest and a small area of the right leg. The patient did not know which ointment was active and which was placebo. During the course of one week 80 g of ointment was applied equivalent to 144 mg of auranofin.

At the end of the first week, a marked improvement in the patient's condition was observed with respect to the areas treated with the active drug. Both patient and attending dermatologist agreed that the improvement was superior to that achieved in the same time interval by any other remedy previously used by this patient. The areas of skin treated with placebo ointment did not improve and may have worsened during the first week.

The patient was then treated with a weaker strength ointment but the condition continued to improve.

Another subject to receive auranofin ointment suffered from mild psoriasis. This person applied the ointment to a small patch of psoriasis and found significant resolution after three days. Beneficial results were also obtained with the other 17 subjects.

Choice of formulation for topical use depends on the type and location of the lesion. The formulation may include stabilizers and/or penetration agents or the like. For general topical use a hydrophobic emulsifiable ointment base produces satisfactory results, however, any other formulation for topical application may be equally applicable, for example monohydric, dihydric and trihydric alkanols. The alcohols may be short chain ($C_1$ to $C_{10}$) alcohols or long chain ($C_{12}$ to $C_{20}$) alcohols.

Especially preferred are polyhydric alcohols such as diethylene glycol or glycerol.

It appears that topical auranofin products should be available in at least two strengths, 0.2% and 0.1%. For maximum effectiveness, additional therapeutic agents may be necessary. For example, where there is intense scaling, prior application of a keratolytic agent may be necessary.

In view of the evidence for synergistic effect between auranofin and corticosteroids, concomitant or sequential use of these agents would seem an appropriate strategy. It would also seem that auranofin applied to skin persists for some time following discontinuation of the drug and thus the synergism between the steroid and auranofin would appear to persist after the auranofin has been discontinued.

Auranofin has features that could make it a very acceptable topical drug if properly formulated. It appears to be very effective as well as being cosmetically acceptable and much easier and more pleasant to use than many of the conventional therapies. It is not possible to give any indication of the likely incidence of adverse effects based on the limited number of cases studied. However its potential risk would seem to be much less than that of other powerful drugs used in the treatment of psoriasis such as methotrexate and etretinate. It would also seem to be more therapeutically effective than these drugs. Although the corticosteroids can be quite effective in psoriasis, the need, in some patients, to use them on a continuous basis carries the risk of skin atrophy plus undesirable systemic effects to which prolonged use on damaged skin can lead.

As will be apparent to those skilled in the art from the teaching hereof, gold compounds other than those exemplified herein may be selected on the basis of their lipid solubility and such compounds, when included in the formulation for topical application, are comprehended within the scope of this invention.

I claim:

1. A topically applied composition comprising:
   a first, active ingredient, component consisting essentially of:
   a sufficient proportion of a lipophilic gold compound to be pharmaceutically active for treatment of disorders of the immune system of skin having the following structure:

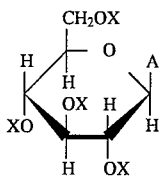

wherein X is H, acetyl or formyl and A is $-S-Au-PR_3$ or $-Y-(CH_2)_n-S-Au-PR_3$; wherein R is substituted or unsubstituted and is at least one member selected from the group consisting of H, alkyl, aryl and heterocyclic; Y is O or S; and n is a number from 1 to 12; and
   a corticosteroid; and
   a second component comprising a sufficient proportion of a pharmaceutically acceptable carrier, having a viscosity greater than water, in combination with said first, active ingredient, component to form a material which is topically applicable to skin;
   wherein said composition has physical properties sufficient to hold it on said skin as a topical application for a time sufficient to enable said active ingredient component to treat said disorder.

2. A composition according to claim 1 wherein the gold compound is:

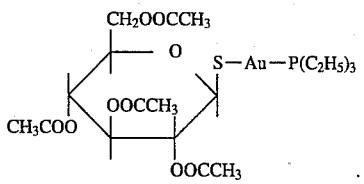

3. A composition according to claim 2 wherein the corticosteroid is betamethasone dipropionate.

4. A composition according to claim 3 wherein the disorder of the skin immune system is psoriasis.

5. A composition according to claim 2 wherein the carrier is an ointment.

6. A composition according to claim 2 wherein the disorder of the skin immune system is psoriasis.

7. A composition according to claim 1 wherein the corticosteroid is betamethasone dipropionate.

8. A composition according to claim 7 wherein the carrier is an ointment.

9. A composition according to claim 7 wherein the disorder of the skin immune system is psoriasis.

10. A composition according to claim 1 wherein the proportion of the gold compound is 0.1% by weight of the total composition.

11. A composition according to claim 1 wherein the proportion of the gold compound is 0.2% by weight of the total composition.

12. A composition according to claim 1 wherein the carrier is an ointment.

13. A composition according to claim 1 wherein the disorder of the skin immune system is psoriasis.

14. A composition according to claim 1 wherein the carrier is an ointment, and the proportion of said gold compound is about 0.05 to 0.25% by weight of said composition.

15. A method of treating an inflamed portion of skin, due to psoriasis, comprising:

forming a pharmaceutical composition comprising:
a first, active ingredient portion consisting essentially of:
a sufficient proportion of a lipophilic gold compound to be pharmaceutically active for treatment of disorders of the immune system of skin which gold compound has a structural formula of:

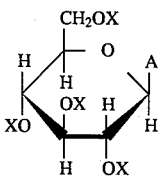

wherein X is H, acetyl or formyl and A is —S—Au—PR$_3$ or —Y—(CH$_2$)$_n$—S—Au—PR$_3$; wherein R is substituted or unsubstituted and is at least one member selected from the group consisting of H, alkyl, aryl and heterocyclic; Y is O or S; and n is a number from 1 to 12; and
a corticosteroid; and
a sufficient proportion of a second component comprising a pharmaceutically acceptable carrier to form a material having physical properties sufficient to be topically applicable to skin;

topically applying said pharmaceutical composition to, or in the area of, a portion of skin suffering from psoriasis; and maintaining said composition on said skin for a time sufficient to enable said gold compound to treat, and to ameliorate the effects of, said psoriasis.

16. A method as claimed in claim 15 wherein said gold compound is:

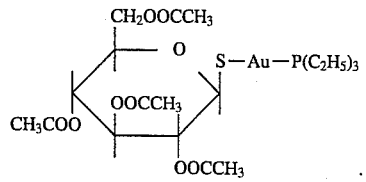

17. A pharmaceutical composition comprising:
a first, active ingredient portion consisting essentially of:
a sufficient proportion of a lipophilic gold compound to be pharmaceutically active for treatment of disorders of the immune system of skin which gold compound has a structural formula of:

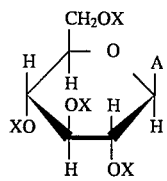

wherein X is H, acetyl or formyl and A is —S—Au—PR$_3$ or —Y—(CH$_2$)$_n$—S—Au—PR$_3$; wherein R is substituted or unsubstituted and is at least one member selected from the group consisting of H, alkyl, aryl and heterocyclic; Y is O or S; and n is a number from 1 to 12; and
a pharmaceutically acceptable carrier sufficient to form a material having physical properties sufficient to be topically applicable to skin and to be held on said skin for a time sufficient to treat said disorder.

18. A composition according to claim 17 wherein the gold compound is:

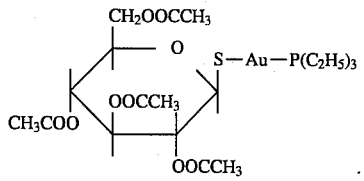

19. A composition according to claim 17 wherein the proportion of the gold compound is 0.1% by weight of the total composition.

20. A composition according to claim 17 wherein the proportion of the gold compound is 0.2% by weight of the total composition.

21. A composition according to claim 17 wherein the carrier is an ointment.

22. A composition according to claim 17 wherein the disorder of the skin immune system is psoriasis.

23. A method of treating an inflamed portion of skin, due to psoriasis, comprising:

forming a pharmaceutical composition comprising:
a first, active ingredient portion consisting essentially of:
a sufficient proportion of a lipophilic gold compound to be pharmaceutically active for treatment of disorders of the immune system of skin which gold compound has a structural formula of:

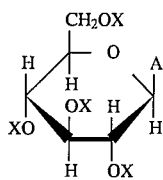

wherein X is H, acetyl or formyl and A is —S—Au—PR$_3$ or —Y—(CH$_2$)$_n$—S—Au—PR$_3$; wherein R is substituted or unsubstituted and is at least one member selected from the group consisting of H, alkyl, aryl and heterocyclic; Y is O or S; and n is a number from 1 to 12; and a pharmaceutically acceptable carrier sufficient to form a material having physical properties sufficient to be topically applicable to skin;

topically applying said pharmaceutical composition to, or in the area of, a portion of skin suffering from psoriasis; and maintaining said composition on said skin for a time sufficient to enable said gold compound to treat, and to ameliorate the effects of, said psoriasis.

24. A method as claimed in claim 23 wherein said gold compound is:

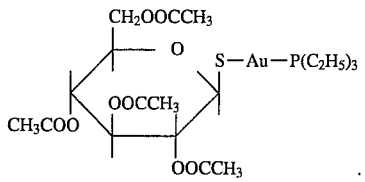

25. A composition according to claim 23 wherein the proportion of the gold compound is 0.1% by weight of the total composition.

26. A composition according to claim 23 wherein the proportion of the gold compound is 0.2% by weight of the total composition.

27. A composition according to claim 23 wherein the carrier is an ointment.

28. A composition according to claim 23 wherein the disorder of the skin immune system is psoriasis.

* * * * *